United States Patent
Patel et al.

(10) Patent No.: US 10,806,850 B2
(45) Date of Patent: Oct. 20, 2020

(54) MEDICAL APPARATUS AND METHOD FOR STERILIZING MEDICAL APPARATUS

(71) Applicant: Bee Sight Limited, Ebene (MU)

(72) Inventors: Timir Patel, Clarksville, MD (US); Harish Patel, Clarksville, MD (US)

(73) Assignee: Bee Sight Limited, Ebene (MU)

( * ) Notice: Subject to any disclaimer, the term of this patent is extended or adjusted under 35 U.S.C. 154(b) by 68 days.

(21) Appl. No.: 15/888,020

(22) Filed: Feb. 3, 2018

(65) Prior Publication Data

US 2018/0221564 A1    Aug. 9, 2018

Related U.S. Application Data

(60) Provisional application No. 62/454,651, filed on Feb. 3, 2017.

(51) Int. Cl.
*A61M 5/00* (2006.01)
*A61L 2/07* (2006.01)
(Continued)

(52) U.S. Cl.
CPC ....... *A61M 5/002* (2013.01); *A61B 17/06114* (2013.01); *A61B 17/3215* (2013.01); *A61L 2/07* (2013.01); *A61L 2/08* (2013.01); *A61L 2/081* (2013.01); *A61L 2/206* (2013.01); *A61M 5/001* (2013.01); *A61M 25/002* (2013.01); *B65B 55/06* (2013.01); *B65B 55/08* (2013.01); *B65B 55/10* (2013.01); *A61B 50/30* (2016.02); *A61L 2/202* (2013.01); *A61L 2/208* (2013.01);
(Continued)

(58) Field of Classification Search
CPC .... A61M 5/002; A61M 5/001; A61M 25/002; A61M 2205/0205; A61L 2/206; A61L 2/08; A61L 2202/182; A61L 2202/23; A61B 17/3215; A61B 17/06114; A61B 50/30; B65D 55/06; B65D 55/08; B65B 55/06; B65B 55/08; B65B 55/04
USPC ................ 206/364, 366, 365, 571, 570, 370
See application file for complete search history.

(56) References Cited

U.S. PATENT DOCUMENTS 4,522,302 A * 6/1985 Paikoff .................. A61B 50/33
                                                         206/216
4,652,763 A    3/1987 Nablo
(Continued)

FOREIGN PATENT DOCUMENTS

| CN | 101851830 B | 10/2010 |
|---|---|---|
| WO | 2010018394 A1 | 2/2010 |
| WO | 2016191535 A2 | 12/2016 |

OTHER PUBLICATIONS

PCT Search Report and Written Opinion (17 Pages).
Co-pending Application No. PCT/US20/26822, International Search Report and Written Opinion dated Jul. 2, 2020.

*Primary Examiner* — Steven A. Reynolds
(74) *Attorney, Agent, or Firm* — Woods Rogers PLC; Nathan A. Evans (57) ABSTRACT

According to the invention, there is provided a medical apparatus including: one or more sterile pre-filled syringe; one or more first protective container including the one or more sterile pre-filled syringe, wherein the one or more first protective container is impermeable to moisture and/or sterilizing agents; a second protective container including one or more medical components and the one or more first protective container; and a package impermeable to bacteria including the second protective container.

45 Claims, 2 Drawing Sheets

(51) Int. Cl.
*A61L 2/08* (2006.01)
*A61B 17/06* (2006.01)
*A61B 17/3215* (2006.01)
*A61L 2/20* (2006.01)
*A61M 25/00* (2006.01)
*B65B 55/06* (2006.01)
*B65B 55/08* (2006.01)
*B65B 55/10* (2006.01)
*B65B 55/12* (2006.01)
*B65B 55/04* (2006.01)
*A61B 50/30* (2016.01)

(52) U.S. Cl.
CPC ... *A61L 2202/181* (2013.01); *A61L 2202/182* (2013.01); *A61L 2202/23* (2013.01); *A61M 2205/0205* (2013.01); *B65B 55/04* (2013.01); *B65B 55/12* (2013.01)

(56) References Cited

U.S. PATENT DOCUMENTS

| | | | |
|---|---|---|---|
| 4,844,259 A * | 7/1989 | Glowczewskie, Jr. | A01N 1/0263 206/370 |
| 5,356,006 A * | 10/1994 | Alpern | B65D 5/302 206/363 |
| 5,718,245 A * | 2/1998 | Horn | A61F 15/001 128/897 |
| 5,997,811 A | 12/1999 | Esposito | |
| 6,691,868 B2 * | 2/2004 | Roshdy | B65D 77/26 206/366 |
| 6,769,546 B2 | 8/2004 | Busch | |
| 2002/0185406 A1 * | 12/2002 | Massengale | A61M 5/002 206/571 |
| 2003/0158512 A1 * | 8/2003 | Lamborne | A61M 5/002 604/26 |
| 2004/0200754 A1 | 10/2004 | Hagemeier | |
| 2005/0092636 A1 * | 5/2005 | Su-Syin | A61L 2/07 206/363 |
| 2005/0268573 A1 | 12/2005 | Yan | |
| 2006/0275336 A1 * | 12/2006 | Du Plessis | A61L 2/0011 424/423 |
| 2006/0283745 A1 * | 12/2006 | Massengale | A61M 5/002 206/438 |
| 2009/0123332 A1 | 5/2009 | Whitehead et al. | |
| 2009/0236259 A1 * | 9/2009 | Hicks | A61B 50/30 206/571 |
| 2011/0297567 A1 * | 12/2011 | Maness | A61M 5/3205 206/366 |
| 2012/0114524 A1 | 5/2012 | Sigg | |
| 2014/0013718 A1 * | 1/2014 | Maasarani | A61M 5/002 53/492 |
| 2016/0347492 A1 | 12/2016 | Lu et al. | |
| 2017/0281876 A1 | 10/2017 | Odell et al. | |
| 2018/0221564 A1 | 8/2018 | Patel et al. | |

\* cited by examiner

MEDICAL APPARATUS AND METHOD FOR STERILIZING MEDICAL APPARATUS

CROSS-REFERENCE TO RELATED APPLICATIONS

The present application relies on the disclosures of and claims priority to and the benefit of the filing dates of U.S. Provisional Application No. 62/454,651, filed Feb. 3, 2017. The disclosures of that application are hereby incorporated by reference herein in their entireties.

BACKGROUND OF THE INVENTION

Field of the Invention

The present invention discloses a method for sterilising medical kits or apparatus, including pre-filled syringes, and also the contents of novel, sterilized medical kits comprising, in part, pre-filled syringes.

Description of Related Art

In medical interventions or procedures, one or more medical devices, pharmaceutical products and/or other apparatus are typically used. Depending on the medical procedure being performed, different products and devices will be employed. In some situations, it may be difficult to predict specifically what types of medical device(s) and/or medicaments will be required at the outset of a medical procedure.

However, for routine procedures, the requirements in terms of the devices and products that will be needed will be more clearly understood. In such situations, in advance of commencement of the medical procedure, medical professionals will typically gather the devices and products that are likely to be used in the course of the procedure. Alternatively, for additional convenience, the devices and products to be employed in a given procedure may be provided in the form of a pre-assembled, pre-sterilised kit or apparatus. An example of such a kit or apparatus is disclosed in WO2004093760, which is incorporated herein by reference.

Examples of commonly used medical kits include a wound care kit, tracheostomy tray, arthroscopy kit, urology irrigation tray, vascular access tray, incision and drainage tray, suture removal kit, saline flush kit, IV start kit, laparoscopy setup pack, TURP pack, ophthalmic pack, biopsy tray, total knee replacement pack, angiography kit, central line kit, PICC trays, C-section setup pack, and cardiac tray.

Such kits may contain a pre-filled syringe. Since their introduction in the 1950s, the use of pre-filled syringes in medicine and surgery has increased significantly. As their name suggests, pre-filled syringes are syringes that are provided to the end user (e.g., medical professionals) pre-filled and ready to use. Depending on the type of product provided in the syringe and its intended application, pre-filled syringes may be provided in sterilised packaging for added convenience to the end user.

While those skilled in the art will be familiar with methods for sterilising pre-filled syringes, the situation becomes more challenging when the pre-filled syringe is provided as part of a medical kit. More specifically, as mentioned above, medical kits are generally provided to the end user in a ready to use, sterilised condition. While the sterilisation of certain components conventionally employed in medical kits may not be problematic owing to their ability to withstand harsh sterilisation conditions, the same may not be true for pre-filled syringes either as a result of the material from which the syringe body is formed, or because of the sensitivity of the product contained within the syringe.

For example, medical devices formed of metal (e.g., scalpels, needles, forceps) may be sterilised via heat, steam, irradiation (e.g., gamma irradiation) or exposure to chemicals (e.g., ethylene oxide, ozone, chlorine, chlorine dioxide, hydrogen peroxide, peracetic acid or nitrogen dioxide). Likewise, products formed of woven or textile materials (e.g., gauzes, bandages) can be sterilised using such techniques without those products being damaged. For example, cellulose based materials are not compatible with $NO_2$ sterilization and require protecting separately.

However, there are also products and devices for which many of these sterilisation approaches will be inappropriate. For example, products which are heat sensitive (e.g., those containing plastic tubes or other components which may be softened or melted at sterilisation temperatures, or pharmaceutical products containing heat sensitive active ingredients) or moisture sensitive (e.g., pharmaceutical products which are hygroscopic or which are packaged in devices comprising leachable components) cannot be sterilised using standard sterilization techniques, such as heat or steam, as prescribed by ISO 17665 Steam Sterilization for Medical Devices.

Accordingly, for entities engaged in the sterilisation of such products and devices (or kits comprising such products and devices), the decision may be taken to employ sterilisation approaches which can be used with moisture- and heat-sensitive devices. An example of such an approach, which is in widespread use and is immediately of interest, is chemical sterilization, i.e. the sterilization of devices using ethylene oxide or alternatively nitrogen oxide, ozone, peracetic acid, chlorine, chlorine dioxide, hydrogen peroxide or other materials with which one skilled in the art will be familiar.

Ethylene oxide is a bactericidal gas which is used widely in the sterilisation of medical devices and products. Sterilisation with ethylene oxide is typically conducted at temperatures in the region of around 40° C. to 60° C. and under vacuum, for example in accordance with standard ISO 11135 ETO Sterilization for Medical Devices. While this sterilisation approach is capable of being used in connection with products and devices that are heat, moisture and irradiation-sensitive, problems may arise when pre-filled syringes are sterilised with ethylene oxide.

The principal concern regarding the use of ethylene oxide sterilisation with pre-filled syringes relates to the ingress of the ethylene oxide into the pre-filled syringe which can contaminate the product within the syringe and lead to unacceptable levels of residual contaminants in that product, especially in the case of products intended for neo-natal and pediatric populations. The concerns regarding the ingress of ethylene oxide into the syringe are especially acute for pre-filled syringes constructed from plastic materials, such as polypropylene, owing to possible leaching of ethylene oxide through the syringe body and contamination of the contents. For example, in US2005/0267423, which is incorporated herein by reference, it is acknowledged that "Ethylene oxide gas can readily penetrate thin layers of most plastics. Once inside, the gas is difficult to dissipate quickly. The interaction of ethylene oxide gas and iodine-containing solutions is that it can result in the formation of additional toxic residues. These contaminants include ethylene oxide (EtO), ethylene chlorohydrin (ECH) and ethylene glycol (EG)." These concerns are not limited to iodine-containing solutions, but can also arise with other aqueous formulations.

Additionally, the concerns regarding the presence of residual ethylene oxide and its contaminants are particularly acute for ready to use kits intended for use in interventions with pediatric or neonatal patients.

Accordingly, for those engaged in providing medical kits and for those that have invested in the costly devices needed to employ ethylene oxide sterilisation, it is not possible to sterilise kits comprising pre-filled syringes in a single sterilisation operation. Conventionally, for such entities which provide pre-sterilised kits comprising pre-filled syringes, the pre-filled syringe is typically separately sterilised from the remainder of the packaged components of the kit using a different sterilisation approach and provided separately and exterior of the packaging containing the remaining components of the kit. Packaging the kit in this way is labor intensive and also risks damage to the externally provided pre-filled syringe during storage and transport of the kit.

A different approach is disclosed in International Patent Publication WO2005/073091, which is incorporated herein by reference. More specifically, in that publication, the device to be sterilized is placed within a package comprising a gas permeable portion. The container is then exposed to a sterilizing gas in order to sterilize the device located therein. Upon completion of the sterilization, the gas permeable portion of the package is sealed or removed, thus protecting the sterilized device located therein from environmental gases or moisture.

However, those skilled in the art will recognize that the approach disclosed in WO2005/073091 does not fully address the problem of the ingress and retention of potentially toxic residual sterilizing gas (or contaminants thereof) as such material could remain present within the container and indeed would be trapped therein upon removal of the gas permeable portion of that container. Further, one skilled in the art will also recognize that the construction of the container will be challenging, resulting in either an increase in the complexity of the manufacture of the container, or (if sourced from a third party supplier) an increase in the cost of each sterilization cycle.

Thus, there remains a need for a process for producing a medical apparatus comprising a pre-filled syringe which can be more simply sterilised in a sterilisation step, regardless of the material from which the syringe is formed or its contents. There is also a need for such a process which can be employed to provide ready to use sterilized apparatus which are free of, or have acceptably low levels of chemical agents used in sterilization, for example ethylene oxide or its contaminants.

SUMMARY OF THE INVENTION

Figure 1:
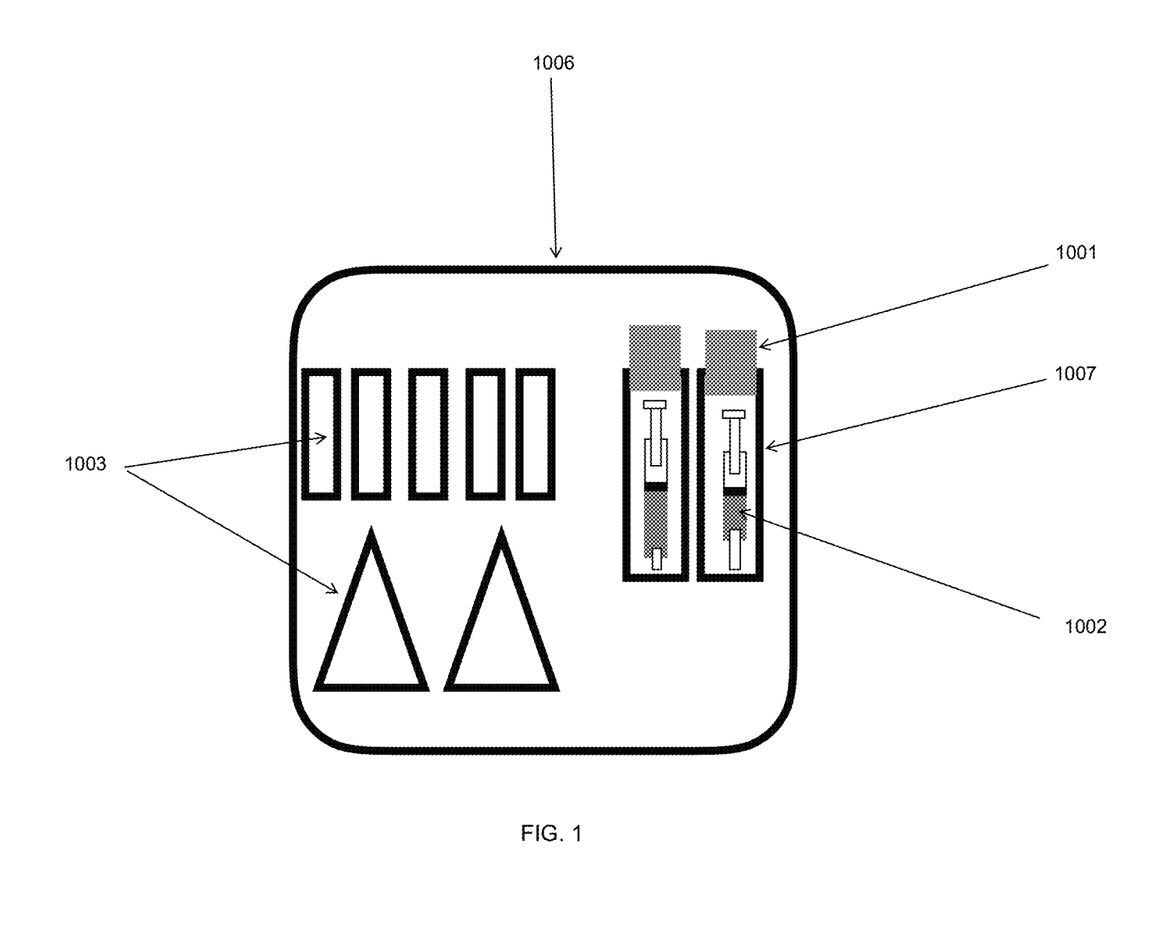
FIG. 1 is a schematic diagram of a depiction of one possible embodiment of a medical apparatus described herein.

According to a first aspect of the present invention, there is provided a process for providing an apparatus comprising i) providing a sterile pre-filled syringe contained within a protective container, which protective container is impermeable to moisture and/or sterilizing agents, ii) providing a kit comprising one or more medical components and the protective container containing the pre-filled syringe, and iii) packaging the kit within a bacterially impermeable package. (See e.g., FIG. 1.)

Also according to the present invention, there is provided a method for providing a medical apparatus, the method comprising: i. providing one or more pre-filled syringe contained within one or more first protective container, wherein the one or more first protective container is impermeable to moisture and/or sterilizing agents; ii. providing a second protective container comprising one or more medical components and the one or more first protective container containing the one or more pre-filled syringe; and iii. packaging the second protective container within a package impermeable to bacteria. (See e.g., FIG. 1.)

Further according to the present invention, there is provided a medical apparatus comprising: one or more sterile pre-filled syringe; one or more first protective container comprising the one or more sterile pre-filled syringe, wherein the one or more first protective container is impermeable to moisture and/or sterilizing agents; a second protective container comprising one or more medical components and the one or more first protective container; and a package impermeable to bacteria comprising the second protective container. (See e.g., FIG. 1.)

Through the use of the process of the present invention, it is possible to assemble an apparatus, comprising a pre-filled syringe, which can be conveniently sterilized in a sterilization step regardless of the material from which the pre-filled syringe is formed or the contents of the pre-filled syringe.

Those skilled in the art will understand the reference to a "sterilisation step" to mean a sterilization process which may comprise a single process step or a number of sequential steps or cycles. "Sterilisation" is a process which results in a reduction in the number of viable microbial contaminants of a medical apparatus, or components thereof.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

In embodiments of the present invention, the process includes a principal sterilization step in which the container comprising the pre-filled syringe is sterilized. In a preferred embodiment, the principal sterilization step, if performed as part of the process of the present invention, is carried out after step ii). In other aspects, this principal sterilization step may be carried out prior to or following step iii) of the process.

In embodiments of the process in which the principal sterilization step is carried out between steps ii) and iii), step iii) preferably takes place in a sterile environment and/or the bacterially impermeable package is sterilized prior to step iii) such that the interior of the bacterially impermeable package is sterilized. In such an embodiment, additional sterilization steps may be performed after step iii) if needed, for example, to extend the shelf life of the apparatus.

In embodiments of the process in which the principal sterilization step is carried out after step iii), the container comprising the pre-filled syringe is preferably not sterilized between steps ii) and iii). Where the principal sterilization step is carried out after step iii) of the process of the present invention, this results in the interior of the bacterially impermeable package (and thus the assembled kit contained within the interior of the bacterially impermeable package) being sterilized.

The principal sterilization step may employ any sterilization approach known to those skilled in the art and which does not result in significant damage or inactivation of any of the components (see, e.g., 1003 in FIG. 1; 2003 in FIG. 2) in the kit. For example, the principal sterilization step may comprise exposing the medical kit to heat, steam (e.g., ISO 17665), irradiation (e.g., gamma irradiation, ISO 11137), nitrogen dioxide (e.g., validated to ISO 14937:2009), and/or ethylene oxide (e.g., ISO 11135). In a preferred embodiment of the invention, the principal sterilization step comprises exposing the kit to ethylene oxide, ozone, chlorine, chlorine dioxide, hydrogen peroxide, peracetic acid and/or nitrogen dioxide.

In embodiments of the invention in which the medical kit is subjected to a principal sterilization step, the residual ETO in the contents of the syringe is about 5 ppm or less, about 2 ppm or less, about 1 ppm or less or about 0.5 ppm or less.

In alternative embodiments of the invention, no principal sterilization step is carried out as part of the process of the present invention. Even if no principal sterilization step is carried out as part of the process of the invention, the process still advantageously results in the provision of a packaged kit that can be readily and easily sterilized in a sterilization step.

Preliminary sterilization steps may be carried out on the medical components (or part/s thereof) and/or the pre-filled syringe (or part/s thereof) prior to step iii) if required. Any sterilization approach may be employed in these preliminary sterilization steps, depending on the device which is to be sterilized. In embodiments of the invention, the preliminary sterilization steps may comprise heat, steam, irradiation (e.g., gamma irradiation), nitrogen dioxide and/or ethylene oxide sterilization.

Regarding step i) of the process of the present invention, this may be achieved by i-a) providing a pre-filled syringe, i-b) placing the pre-filled syringe (see, e.g., 1002 in FIG. 1) within the protective container (see 2005 in FIG. 2), and i-c) sealing the protective container. In such embodiments, the pre-filled syringe may be subjected to a preliminary sterilization step (for example a heat, steam, irradiation (e.g., gamma irradiation), or nitrogen dioxide sterilization step) prior to closure of the protective container (e.g., between steps i-b) and i-c) and/or following step i-c). In embodiments, at or around step 2005 of FIG. 2, related steps may be performed under sterile, clean conditions; and other sterilisation steps may be performed before closure with the stopper or other closing and/or sealing mechanism, instrument, and/or procedure, and optional further gamma irradiation of the container with the prefilled syringe is also an option. In preferred embodiments, a stopper or other way of closing or sealing is made of material, preferably elastomeric, which has a close, secure fit to or with the container inner surface, and can be inserted without forming any defects, which may cause sterilising gas to enter. In preferred embodiments, the stopper or closure should not change any dimensions or become degraded during or after the sterilising conditions. Further, the stopper or closure should preferably be readily removable at point of use (e.g., by a clinician).

In such an embodiment, in step i-a), the pre-filled syringe may be provided by providing an unfilled syringe, optionally sterilizing the unfilled syringe (for example, with heat, steam, irradiation (e.g., gamma irradiation), nitrogen dioxide, and/or ethylene oxide), and filling the syringe. (See 2004 in FIG. 2.) Alternatively, the pre-filled syringe may be provided by providing the component parts of the syringe, optionally sterilizing the component parts of the syringe (for example, with heat, steam, irradiation (e.g., gamma irradiation), and/or chemical sterilizing agents (e.g., ethylene oxide, ozone, chlorine, chlorine dioxide, hydrogen peroxide, peracetic acid and/or nitrogen dioxide)), assembling the syringe, optionally sterilizing the assembled syringe (for example, with heat, steam, irradiation (e.g., gamma irradiation), and/or chemical sterilizing agents (e.g., ethylene oxide, ozone, chlorine, chlorine dioxide, hydrogen peroxide, peracetic acid, and/or nitrogen dioxide)), and filling the syringe. The syringe may be "naked" (e.g., not in a container or package) or already in a container, package, and/or a sealed container or package. (See 2005 in FIG. 2.)

The protective container (see, e.g., 1007 in FIG. 1; 2007 in FIG. 2) may take any form and be formed of any material provided that it prevents the pre-filled syringe contained therein from being rendered inutile during a subsequent sterilization step. It preferably comprises a body and a closure, for example a lid, stopper or cap. In preferred embodiments, the stopper is ethylene oxide proof (or highly resistant) and/or removable. (See, e.g., 1001 in FIG. 1; 2001 in FIG. 2.) In embodiments of the invention, the protective container, when closed, may be impermeable to moisture and/or sterilizing agents, such as ethylene oxide, ozone, chlorine, chlorine dioxide, hydrogen peroxide, peracetic acid, and/or nitrogen dioxide. In preferred embodiments, the protective container, when closed, is impermeable to ethylene oxide. In embodiments, the protective container and a stopper or other way of closing and/or sealing the protective container is sterilized inside and out before a pre-filled syringe is put into the protective container. (See 1007 in FIG. 1; 2007 in FIG. 2 (e.g., with gamma irradiation)).

In embodiments of the invention, prior to step i-c), the prefilled syringe may first be packaged into its own syringe packaging, for example, a sheath, envelope, or wrapper, and optionally sealed therein. (See, e.g., 2004 in FIG. 2.) In such embodiments, the pre-filled syringe may optionally be subjected to one or more preliminary sterilization steps which are carried out before and/or after sealing of the syringe packaging, but preferably prior to step i-c). In embodiments in which the prefilled syringe is provided with syringe packaging, this may bear information regarding the prefilled syringe and/or its contents, for example one or more of a label, date of manufacture, batch number, active ingredient, composition, bar code containing information of use/date/name of patient and/or user of that batch, or the like.

Examples of materials from which the protective container may be formed include glass, polymers such as polyolefins, cyclic olefin copolymer, polycarbonate, $SiO_2$ coated polymer, polyethylene (e.g., high density polyethylene), metal foil covered plastic, ceramics, metals such as aluminum, and/or composites of two or more of these materials. In embodiments of the invention, the protective container is partially or totally formed of reusable, recyclable and/or compostable material, and/or renewable or fossil oil based raw materials.

In embodiments of the invention, the protective container may be coated and/or the material from which it is produced formulated to achieve the requisite impermeability to sterilisation conditions.

In embodiments of the invention, the closure of the protective container may be irreversibly separable from the remainder of the protective container. For example, the closure of the container may be formed from the same (or different) material as some or all of the container body but the closure may be defined by a weakened portion of material (e.g., a tear line), facilitating removal of the closure from the container body, e.g., by tearing the closure from the body. This type of closure is preferred in order to ensure the sterilizing material does not ingress into the container.

In some embodiments of the invention, the closure may be mechanically coupled to the body of the protective container, e.g., by friction fit, push-fit, interlocking means, threaded means, or the like.

The closure of the protective container may be provided with means to facilitate its removal from the body of the protective container, for example a tab, a pull, knurling, or the like.

In embodiments in which the pre-filled syringe is subjected to a preliminary sterilization step, this may be before or after it is placed in the protective container. For example, the pre-filled syringe may be subjected to a sterilization step (for example, using heat, steam, irradiation (e.g., gamma irradiation), and/or nitrogen dioxide) and then placed in to the protective container preferably in a sterile environment, and the protective container then closed. In embodiments, the container may be flushed with an inert gas, such as nitrogen, prior to closing and/or sealing.

Such operations will usually be performed in a controlled environment such as a sterile room or cabinet (such as a fume cupboard) in accordance with legislative and regulatory guidelines (e.g., class 100 (ISO 5) environments) which should normally minimise the presence of, or ideally yield no, microbiological contaminants.

Alternatively, the pre-filled syringe may be placed into the protective container and the closure means optionally partially closed (such that the container is not totally sealed). The protective container and pre-filled syringe may then conveniently be sterilized in a single sterilization operation, e.g., using heat, steam, irradiation (e.g., gamma irradiation), and/or nitrogen dioxide, prior to closure of the protective container.

The process of the present invention may additionally comprise the step of applying a supplementary barrier to the protective container. The purpose of this is to provide additional protection to the pre-filled syringe to prevent it being rendered inutile in any subsequently performed sterilization step. The supplementary barrier may be applied to some or all of the protective container. In preferred embodiments, the supplementary barrier is provided at least to the closure of the container and a region of the container adjacent to the closure. In other embodiments, the supplementary barrier may additionally comprise compounds which absorb or react with the sterilizing gas, e.g. ethylene oxide, so that the container is made impermeable to said sterilizing gas.

Any material which enhances the barrier properties of the protective container may be employed as a supplementary barrier in the process of the present invention. For example, the supplementary barrier may be a metallic foil, polymeric film, or the like. In preferred embodiments, the supplementary barrier is an aluminum foil (see, e.g., 2008 in FIG. 2).

Additionally or alternatively, the supplementary barrier may be provided with an adhesive to facilitate intimate contact with the protective container. In such embodiments, during application of the supplementary barrier to the protective container, the supplementary barrier is adhered to the protective container. The barrier and/or adhesive may additionally comprise chemical compounds or other ways to trap or scavenge any ingressed sterilizing gas.

Figure 2:
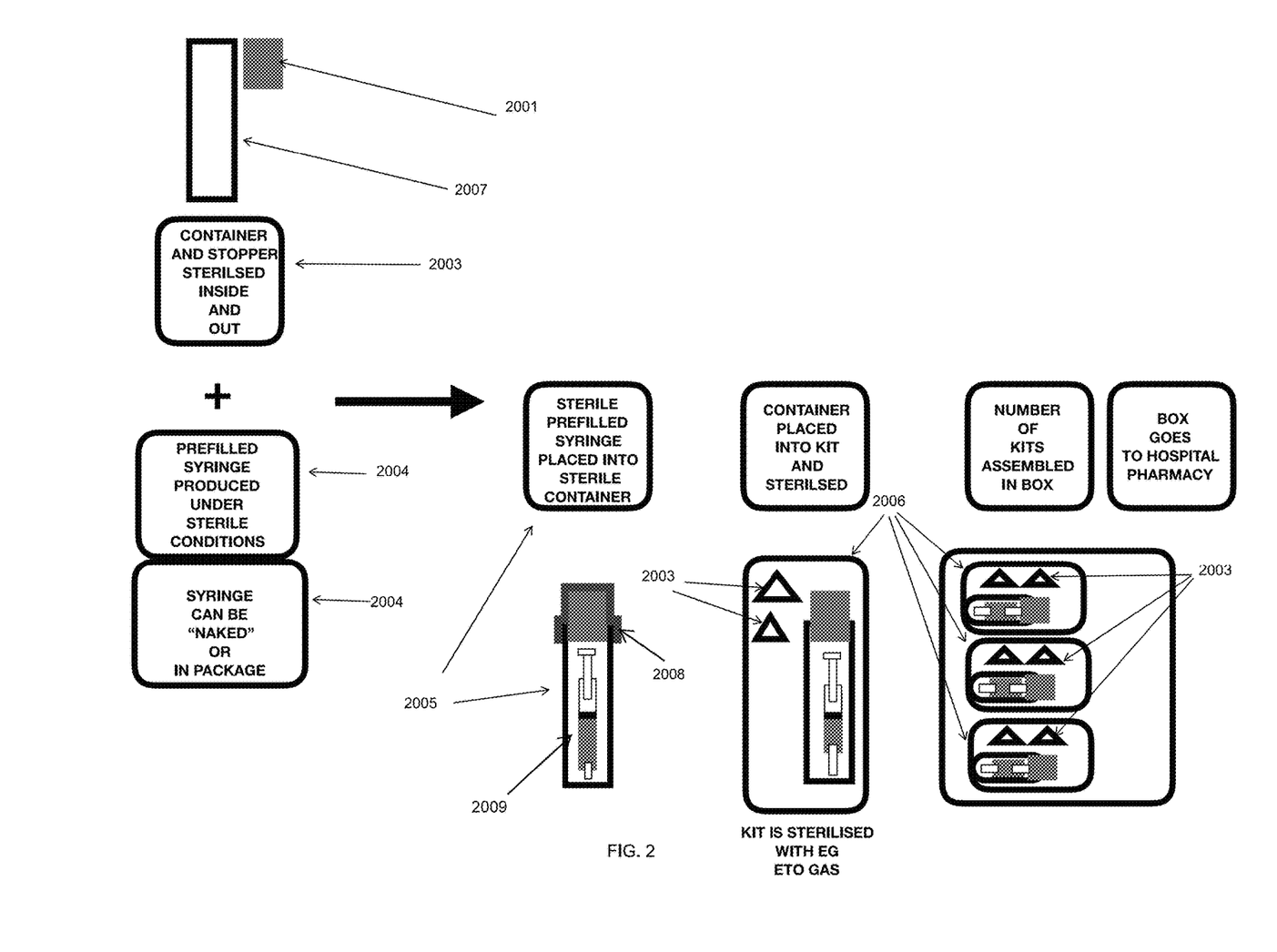
FIG. 2 is a schematic diagram of a depiction of one possible embodiment of a process to prepare a medical apparatus described herein.

Additionally or alternatively, the interior of the protective container may comprise an ethylene oxide scavenger (see, e.g., 2009 in FIG. 2). As its name suggests, the purpose of the ethylene oxide scavenger is to capture any ethylene oxide that ingresses into the protective container and prevent it from contaminating the pre-filled syringe or other components contained therein.

In some embodiments, the ethylene oxide scavenger may be a material which converts ethylene oxide into a harmless material and/or which entraps, co-ordinates, or adheres to ethylene oxide, thus rendering it harmless. Ethylene oxide is highly reactive and undergoes reactions with a variety of compounds: preferably these compounds are such that a reaction with any ethylene oxide converted to harmless materials is of little concern to the contents of the protective container. Examples of such compounds (which may be used as ethylene oxygen scavengers in the present invention) include, but are not limited to, water, alcohols, amines, halides, organometallic compounds, cyanides, sulphides, nitrous or nitric acids, and/or compounds comprising active methylene groups.

Examples of compounds which may be employed as ethylene oxide scavengers include alkaline compounds, for example salts of carboxylic acid; co-ordinating ligands such as EDTA or derivatives thereof; buffered amine solutions; and/or alcohol.

The ethylene oxide scavenger may be provided on and/or impregnated in a substrate, for example one which maximizes the surface area of the ethylene oxide scavenger, such as a woven (e.g., a gauze or gauze-like material) or sponge-like material.

In embodiments of the invention, the ethylene oxide scavenger may be located in a region of the container where ethylene oxide is most likely to be found. For example, in the situation where the protective container takes the form of a lidded container, the ethylene oxide scavenger may be located in the region of the margin between the lid and the container.

The use of an ethylene oxide scavenger may be of particular interest to those engaged in the packaging of surgical kits intended for use in procedures to be conducted on pediatric or neonatal patients, for which restrictions on the tolerable levels of ethylene oxide are more stringent.

In embodiments of the invention, the interior of the container may be provided with antimicrobial agents or other ways to perform sterilization of the container. Such agents or procedures may comprise an antimicrobial agent, for example silver compounds such as nano-silver and/or silver nitrate; alcohols; and/or high molecular weight amines. Additional examples of antimicrobial agents which may be employed as antimicrobial agents in the present invention are disclosed in paragraphs [0121] to [0150] of U.S. Patent Publication No. 2012/0283693, the contents of which are incorporated by reference.

In embodiments of the invention, both an antimicrobial agent and an ethylene oxide scavenger are provided in the interior of the protective container. In certain such embodiments, the antimicrobial agent and the ethylene oxide scavenger are the same material or product.

In embodiments, an antimicrobial agent and/or an ethylene oxide scavenger may be provided in the vicinity of the opening of the protective container. The antimicrobial agent and/or an ethylene oxide scavenger may also be provided within a component of the pre-filled syringe, for example a cap protecting the luer of the syringe.

In embodiments in which both an antimicrobial agent and an ethylene oxide scavenger are provided in the interior of the protective container, the antimicrobial agent and the ethylene oxide scavenger may both be provided on and/or impregnated in a substrate.

Those skilled in the art will be familiar with the construction of syringes that may be employed in the kits. One advantage of the process and kit of the present invention is that the user of the process and kit is not constrained to selecting a syringe formed from only a limited number of materials. Thus, in embodiments of the invention, the syringe body may be formed of glass, polyethylene (e.g., high density polyethylene), polypropylene (e.g., medical grade radiation stable polymer), cyclo olefin polymer or cyclo olefin copolymer (e.g., Topas), or $SiO_2$ coated polymer.

In one aspect, the protective container provided in step i) of the process of the present invention comprises one pre-filled syringe. In embodiments of the invention, the protective container may comprise a plurality of pre-filled syringes, e.g., 2, 3, 4, 5, 6 or more than 6.

The syringe included in the kit may be filled with any material that may be usefully employed in surgery or other medical procedures. For example, the syringe may be pre-filled with saline, e.g., a flush syringe.

Alternatively, the prefilled syringe could be filled with a lock solution which can be used to maintain sterility in devices such as catheters between uses. Examples of lock solutions include lower alcohols, such as ethanol, propanol and/or butanol. In embodiments, the lock solution may also comprise an antimicrobial (such as taurolidine and/or triclosan) and or an anticoagulant (such as riboflavin, sodium citrate, ethylene diamine tetraacetic acid, and/or citric acid).

Alternatively, the prefilled syringe may be pre-filled with an active pharmaceutical composition. The active pharmaceutical composition may be heat sensitive (e.g., which may be denatured and rendered inutile) at temperatures in excess of about 50° C., about 60° C., about 70° C., about 80° C., about 90° C., or about 100° C.

In step ii) of the process, another protective container, also referred to herein as a kit, is provided comprising the protective container housing the pre-filled syringe and one or more other medical components. (See 1006, in FIG. 1; 2006 in FIG. 2.) The identity of the other components will depend on the procedure for which the kit or apparatus is intended to be used. However, there are no particular limitations on the identity of the other components. The second protective container may, in embodiments, with its cover open, be placed into an ETO chamber and sterilised with ETO or other sterilization techniques. The ETO cycle may include aeration and vacuum steps to remove residual ETO. The kit may be closed and/or sealed and optionally further ETO sterilization, or other sterilization, of the closed and/or sealed kit may be performed.

In embodiments of the invention, the other components are selected from one or more of the following: scalpels, needles, forceps, sutures, gauzes, bandages, catheter pads, face masks, IV bag holder, needle foam positioning, prep sponges, Prevantics® pads, swab sticks, syringes, tourniquets and wallet exam gloves.

The medical kit provided in step ii) of the process of the present invention may additionally comprise a packaging base which is configured to retain some or all of the components of the kit (including the protective container) thus preventing them from moving freely within the packaging during transport and handling of the kit, in order to minimise the risk of damage.

In embodiments, the medical kit may comprise a plurality of protective containers in the kit, for example, 2, 3, 4, 5, 6, 7, 8, or more than 8. In such embodiments all of the pre-filled syringes within the protective container may comprise the same formulation and/or comprise the same volume of formulation. Alternatively, in embodiments in which the kit comprises a plurality of containers, the pre-filled syringes contained within those containers may vary in terms of the formulations comprised therein and/or in terms of the volume of formulation comprised therein.

In embodiments in which the kit comprises a plurality of protective containers, the containers and/or the packaging base may be numbered or labelled to facilitate the correct and consistent positioning of the containers within the kit. The additional protective containers may be sterilized and/or constructed as discussed herein.

The medical components and/or the retaining base may independently be subjected to preliminary sterilization steps (for example, with heat, steam, irradiation (e.g., gamma irradiation), and/or chemical sterilizing agents (e.g., ethylene oxide, ozone, chlorine, chlorine dioxide, hydrogen peroxide, peracetic acid, and/or nitrogen dioxide)) prior to step ii) of the process of the present invention.

In step iii) of the process of the present invention, the kit or second container is packaged within a bacterially impermeable package. The package may be formed of any material provided that it is capable of providing a sterile enclosure containing the medical kit. In embodiments, the package is capable of preventing microbial penetration. Examples of bacterially impermeable packaging which may be employed in step iii) of the process of the present invention include, but are not limited to, woven or non-woven materials.

Examples of non-woven package materials that may be employed include polymeric (e.g., cellulose and/or polypropylene-based packaging wraps) which include materials made from renewable, recyclable material, such as bioplastics from starches, cellulose and/or biopolymers. In embodiments, the package is formed of a single or multi-laminate packaging material comprising one or more polypropylene layers. For example, the packaging material may be a multilaminate wrap comprising 1, 2, 3, or more than 3 polypropylene layers. In such embodiments, one or more of the polypropylene layers may be spunbonded, and/or one or more of the propylene layers may be meltblown. Examples of such packaging materials that may be employed in the process of the present invention include, but are not limited to, trilaminates in which the upper and lower layers (i.e., the outer layers) are spunbonded polypropylene and the inner layer is meltblown polypropylene. Such trilaminates will be known to those skilled in the art as 'SMS' materials. Such trilaminates may be used in a single layer arrangement, or multi-layered arrangement, e.g. comprising 1, 2, 3, or more than 3 layers of the trilaminate, optionally with the layers of trilaminate being bonded, fused or otherwise sealed or adhered to each other.

The single layered or multilaminate packaging materials that may be employed in the process of the present invention include those commercialized by Halyard under the trade name Kimguard, by Cardinal Health under the trade name Sterilization Wrap, and by Ahlstrom Fabrics under the name Med-Con.

An example of a woven material that may be employed is muslin, optionally multiple wrapped (e.g., double, sequential wrapped) muslin, and/or polyester-cotton blends which are optionally chemically treated.

The step of packaging the kit may be achieved by surrounding the kit with the packaging material and sealing the packaging material (e.g., via heat sealing, adhesion, or the like) to close the package around the kit. In embodiments, the packaging material may conveniently be provided in the form of a bag into which the kit can be placed, and the bag then sealed (e.g., via heat sealing or using adhesive).

In an embodiment, the packaging material is impermeable to sterilization media (e.g., steam and/or chemical sterilizing agents (e.g., ethylene oxide, ozone, chlorine, chlorine dioxide, hydrogen peroxide, peracetic acid, and/or nitrogen dioxide)). In this embodiment, the packaging material is partially closed during sterilization to allow the sterilisation medium to sterilize the inside of the packaging. After sterilization has taken place, the packaging material is fully closed and/or sealed.

The packaging material is preferably permeable to sterilization media (e.g., heat, steam, gamma irradiation, and/or chemical sterilizing agents (e.g., ethylene oxide, ozone, chlorine, chlorine dioxide, hydrogen peroxide, peracetic acid, and/or nitrogen dioxide)), such that sterilization of the entirety of the packaged medical kit can be conveniently sterilized in a sterilization step. Sterilisation may be carried out before the packaging material is closed. In preferred embodiments, the bacterially impermeable package is permeable to sterilizing gas, for example ethylene oxide.

In embodiments of the invention, the package also exhibits one or more of the following properties: aeratability (e.g., the package permits aeration post sterilisation for example to dissipate ethylene oxide), low or no toxicity, minimal wrap memory, drapeability (such that the package conforms to the kit), flexibility, puncture resistance, tear resistance, low or no odour, low or no linting, and/or conformity with waste disposal regulation.

Upon completion of step iii) of the process of the present invention, the packaged kit may be subjected to one or more supplementary packaging steps, e.g. to provide the kit in packaging which provides greater protection during transit and/or which displays product information to the end user of the overall apparatus.

In embodiments of the invention, the kit may be subjected to an evacuation step, to remove traces of ethylene oxide from the kit prior to and/or following closure of the packaging material in step iii).

In embodiments of the invention, the kit additionally comprises instructions for use. These instructions may provide medical professionals with guidance as to how the medical kit should be employed, for example in procedures to be carried out on pediatric or neonatal patients.

Increasingly bar coded information is used in hospitals to track contents, use and users of the kits, and their components. Accordingly, in aspects of the invention, identification means such as bar code labels may be provided to the kit and/or its contents for ready capture of information into a readable format, e.g. on a computer screen.

Additionally or alternatively, particularly in embodiments of the invention in which a principal sterilization step is not performed, the instructions may provide guidance as to how the medical kit may be sterilized. For example, if the medical kit packaged in step iii) is made in whole or in part of ethylene oxide permeable packaging, the instructions may provide guidance as to how ethylene oxide sterilization may be performed on that packaged medical kit.

The invention will now be discussed with reference to the following examples.

Example 1

A syringe having a polypropylene body was filled with 20 ml sterile 0.9% saline solution compliant with the US Pharmacoepia. The syringe was then packaged in a protective container (glass vial) together with an ethylene oxide (ETO) detector strip (which is red at the start and turns green on exposure to ETO). The vial was then stoppered tightly with a rubber stopper and a ring pull over holder. There existed a tight fit of the stopper without defects so that the ETO sterilant will not ingress.

As a supplementary barrier, an optional aluminum foil was applied over the stopper of the vial and also over the crevice at the boundary of the cap and the vial. The foil was tightly wrapped around the protective container and was additionally provided with adhesive to ensure an intimate and durable connection with the protective container.

A kit comprising the protective container was then assembled and packaged in a surgical wrap material comprising two layers of SMS bonded to each other.

The kit was placed in a chamber 3M Steri-Vac 8XL ETO Gas Sterilizer and ETO was introduced as shown below.

STERILIZATION TEMPERATURE: 55 C
ETO EXPOSURE: 7 HOURS WITH THEORETICAL ETO GAS CONCENTRATION 759 mg/l
AERATION TEMPERATURE: 55 C
AERATION TIME: 54 HOURS

The ETO detector strip remained red.

It is envisaged that when such a kit is sterilized, residual ETO levels of the contents of the syringe will be about 5 ppm or less, more preferably about 1 ppm or less or most preferably about 0.5 ppm or less.

Several further combinations of syringe(s) in various containers and closures were tested for the effect(s) of various glass and aluminum containers and various closure means.

Some observations were noted:

the closure means for the container should be robustly and smoothly fitted so that all sources of defects (however small) caused by the closing technique are avoided. Otherwise, the ETO ingresses readily into the interior of the container and inevitably into the contents of the pre-filled syringe;

amongst various closures tested, the elastomeric stopper was found to be insertable and enabled prevention of any ETO ingress. Stringent closure is required to achieve the very low value (e.g., less than 5 ppm, less than 1 ppm, or less) of ETO ingress required for some of the pre-filled syringe products; and glass and/or aluminum containers are preferred.

Example 2

The following are examples of steps to prepare kits for an end user.

| Embodiment A | Embodiment B | Embodiment C | Embodiment D |
|---|---|---|---|
| Syringe ("syr") exposed to Primary Sterilization cycle only | Syringe exposed to ETO as Secondary (Final) Sterilization Step | Syringe exposed to ETO as Tertiary (Final) Sterilization Step | Syringe exposed to ETO as Tertiary (Final) Sterilization Step |
| NS PP Syr + NS Tip Cap + Sterile 0.9% Sod Chloride USP | NS PP Syr + NS Tip Cap + Sterile 0.9% Sod Chloride USP | NS PP Syr + NS Tip Cap + Sterile 0.9% Sod Chloride USP | Prefilled flush syringe from market |
| Fill <1 ml up to 20 ml into PP Syr via pump-->push saline into syr; Pull force-->pull plunger up to suck saline in; | Fill <1 ml up to 20 ml into PP Syr via pump-->push saline into syr; Pull force-->pull plunger up to suck saline in | Fill <1 ml up to 20 ml into PP Syr via pump-->push saline into syr; Pull force-->pull plunger up to suck saline in | (May be, for example, sterilized via irradiation, steam, autoclave or dry/moist heat or other means) |
| Overwrap syr w/dust cover or in pouch made of moisture barrier film via FFS machine. | Place Syr in container (metal or glass); Place cap (metal, glass or HDPE) over mouth of container; Cover entire cap with foil including crevice near container/cap interface. | Overwrap syr w/dust cover or in pouch made of moisture barrier film via FFS machine. | |
| Place in IC: 100 dust cover or 60 FFS syringes placed into thin walled IC | Place in IC: approx 60 syringes placed into thin walled IC | Place in IC: approx 60 syringes placed into thin walled IC | |
| Place 4 XIC into SC; A thicker walled corrugate case | Place 4XIC into SC; A thicker walled corrugate case | Place 4XIC into SC; A thicker walled corrugate case | |
| Sterilize via: Irradiation. (Primary Sterilization) | Sterilize via: Irradiation. (Primary Sterilization) | Sterilize via: Irradiation. (Primary Sterilization) | |
| | | Remove syringe from outer covering and place Syr in container (metal, or glass) | Remove syringe from outer covering and place Syr in container (metal or glass); |
| | | Sterilize via NO2 (Noxilizer Technology); Or Steam sterilization; or dry/moist heat other method; (Secondary Sterilization) | Sterilize via NO2 (Noxilizer Technology); Or Steam sterilization; or dry/moist heat or other method; (Secondary Sterilization) |
| | | Place cap (metal, glass or HDPE) over mouth of container; Cover entire cap with foil including crevice near container cap interface. | Place cap (metal, glass or HDPE) over mouth of container; Cover entire cap with foil including crevice near container cap interface. |
| | | Place in IC: approx 60 syringes placed into thin walled IC | Place in IC: approx 60 syringes placed into thin walled IC |
| | | Place 4XIC into SC; A thicker walled corrugate case | Place 4XIC into SC; A thicker walled corrugate case |
| Customer pre-packs kits | Customer pre-packs kits including ETO impermeable container with 0.9% Sodium Chloride flush. | Customer pre-packs kits including ETO impermeable container; with 0.9% Sodium Chloride flush. | Customer pre-packs kits including ETO impermeable container; with 0.9% Sodium Chloride flush. |
| Kit sterilized via ETO | Kit sterilized via ETO; (Secondary Sterilization) | Kit sterilized via ETO; (Tertiary Sterilization) | Kit sterilized via ETO; (Tertiary Sterilization) |

-continued

| Embodiment A | Embodiment B | Embodiment C | Embodiment D |
| --- | --- | --- | --- |
| Post ETO sterilization: 0.9% Sodium Chloride Syr is piggy backed onto each kit in a protective sleeve. Potential Tube Embodiments: | | | |
| Sodium Chloride (0.45%; 0.9%; 3%; 6%) Lidocaine for inj 1%-2%; Epinephrine for inj 1:1000 | | | |

Acronym Key:
NS = Non-Sterile;
PP = Polypropylene;
IC = Intermediate Case;
SC = Shipper Case One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for providing a medical apparatus, the method comprising:
   i. providing one or more sterilized pre-filled syringe contained within one or more first protective container, wherein the one or more sterilized pre-filled syringe is completely or partially filled with a sterilized liquid for injecting into a human or animal, wherein the liquid reacts with ethylene oxide gas, and wherein the one or more first protective container is impermeable to moisture and/or sterilizing agents;
   ii. providing a second protective container comprising one or more medical components and the one or more first protective container containing the one or more sterilized pre-filled syringe, wherein the second protective container is sterilized using ethylene oxide gas; and
   iii. sterilizing the second protective container with the ethylene oxide after the one or more first protective container containing the one or more sterilized pre-filled syringe is placed into the second protective container.

2. The method of claim 1, wherein the sterilizing agents are chosen from one or more of ethylene oxide, ozone, chlorine, chlorine dioxide, hydrogen peroxide, peracetic acid, and/or nitrogen dioxide.

3. The method of claim 1, further comprising sterilizing the second protective container before the one or more first protective container containing the one or more sterilized pre-filled syringe is placed into the second protective container.

4. The method of claim 1, further comprising sterilizing the combined one or more pre-filled syringe contained within the one or more first protective container.

5. The method of claim 1, wherein the sterilizing of the second protective container is performed by additionally exposing the second protective container to one or more chemical sterilizing agents selected from one or more of ozone, chlorine, chlorine dioxide, hydrogen peroxide, peracetic acid, and/or nitrogen dioxide.

6. The method of claim 1, wherein the one or more first protective container is additionally sterilized after the second protective container is sterilized.

7. The method of claim 4, further comprising additionally sterilizing the second protective container before the one or more sterilized pre-filled syringe contained within the one or more first protective container is placed into the second protective container.

8. The method of claim 1, wherein step i. comprises:
   i-a) providing the one or more sterilized pre-filled syringe,
   i-b) placing the one or more sterilized pre-filled syringe within the one or more first protective container, and
   i-c) sealing the one or more first protective container.

9. The method of claim 8, wherein the one or more pre-filled syringe is sterilized prior to placing the one or more sterilized pre-filled syringe within the one or more first protective container.

10. The method of claim 8, wherein prior to sealing the one or more first protective container, the one or more first protective container is sterilized.

11. The method of claim 8, wherein prior to sealing the one or more first protective container, the one or more first protective container and the one or more sterilized pre-filled syringe are sterilized.

12. The method of claim 8, wherein prior to sealing the one or more first protective container, the one or more first protective container and the one or more sterilized pre-filled syringe are sterilized at the same time.

13. The method of claim 1, wherein the one or more first protective container and/or the one or more sterilized pre-filled syringe are sterilized using heat, steam, irradiation, and/or nitrogen dioxide.

14. The method of claim 1, wherein the one or more first protective container comprises a supplementary barrier.

15. The method of claim 14, wherein the supplementary barrier is adhered to the one or more first protective container.

16. The method of claim 1, wherein an interior of the one or more first protective container comprises an ethylene oxide scavenger and/or antimicrobial agent.

17. The method of claim 16, wherein the ethylene oxide scavenger and/or the antimicrobial agent are provided on and/or impregnated in a substrate.

18. The method of claim 1, wherein the second protective container comprises a packaging base.

19. The method of claim 1, wherein the one or more first protective container comprises one or more of:
   glass;
   one or more polymer chosen from polyolefins, cyclic olefin copolymer, polycarbonate, $SiO_2$ coated polymer, polyethylene, and/or plastic completely or partially covered in metal;
   ceramic; and/or
   metal.

20. The method of claim 1, wherein the one or more first protective container comprises one or more of:
   reusable, recyclable, and/or compostable material(s); and/or
   renewable or fossil oil based raw material(s).

21. The method of claim 1, wherein the one or more first protective container is coated with one or more of:
   moisture resistant agent(s);
   moisture impermeable agent(s); and/or
   sterilization impermeable agent(s).

22. A medical apparatus comprising:
   one or more sterile pre-filled syringe completely or partially filled with a liquid capable of treating a human or animal, wherein the liquid negatively reacts with ethylene oxide gas;
   one or more first protective container comprising the one or more sterile pre-filled syringe, wherein the one or more first protective container is impermeable to moisture and/or sterilizing agents and comprises an impermeable, removable, sterile cap; and
   a second protective container comprising one or more medical components and the one or more first protective container, wherein the second protective container and the one or more medical components are sterilized by ethylene oxide gas;
   wherein the second protective container is sterilized with the ethylene oxide gas and sealed after the first protective container comprising the sterile pre-filled syringe is placed within a cavity of the second protective container.

23. The medical apparatus of claim 22, wherein the one or more medical components are chosen from one or more of scalpels, needles, forceps, sutures, gauzes, bandages, catheter pads, face masks, IV bag holder, needle foam positioning, prep sponges, Prevantics® pads, swab sticks, syringes, tourniquets, and/or wallet exam gloves.

24. The medical apparatus of claim 22, wherein the sterilizing agents are chosen from one or more of ethylene oxide, ozone, chlorine, chlorine dioxide, hydrogen peroxide, peracetic acid, and/or nitrogen dioxide.

25. The medical apparatus of claim 22, wherein the one or more first protective container is sterilized.

26. The medical apparatus of claim 22, wherein the second protective container is additionally sterilized with one or more chemical sterilizing agents selected from one or more of ozone, chlorine, chlorine dioxide, hydrogen peroxide, peracetic acid, and/or nitrogen dioxide.

27. The medical apparatus of claim 22, wherein the one or more first protective container is sterilized and, wherein the one or more sterile pre-filled syringe contained within the one or more first protective container is sterilized before, after, and/or at the same time as the one or more first protective container is sterilized.

28. The medical apparatus of claim 22, wherein the one or more first protective container and the second protective container are sterilized and, wherein the one or more first protective container is sterilized before, after, and/or at the same time as the second protective container is sterilized.

29. The medical apparatus of claim 22, wherein the one or more sterile pre-filled syringe is sterilized prior to placing the one or more sterile pre-filled syringe within the one or more first protective container.

30. The medical apparatus of claim 22, wherein the one or more sterile pre-filled syringe is sterilized at the same time as the one or more sterile pre-filled syringe is placed within the one or more first protective container and as the one or more first protective container is sterilized.

31. The medical apparatus of claim 22, wherein prior to sealing the one or more first protective container, the one or more first protective container is sterilized.

32. The medical apparatus of claim 22, wherein prior to sealing the one or more first protective container, the one or more first protective container and the one or more sterile pre-filled syringe are sterilized.

33. The medical apparatus of claim 22, wherein the one or more first protective container and the one or more sterile pre-filled syringe are sterilized using heat, steam, irradiation, and/or nitrogen dioxide.

34. The medical apparatus of claim 22, wherein the one or more first protective container comprises a supplementary barrier.

35. The medical apparatus of claim 34, wherein the supplementary barrier is adhered to the one or more first protective container.

36. The medical apparatus of claim 22, wherein an interior of the one or more first protective container comprises an ethylene oxide scavenger and/or antimicrobial agent.

37. The medical apparatus of claim 36, wherein the ethylene oxide scavenger and/or the antimicrobial agent are provided on and/or impregnated in a substrate.

38. The medical apparatus of claim 22, wherein the second protective container comprises a packaging base.

39. The medical apparatus of claim 22, wherein the one or more first protective container comprises one or more of:
   glass;
   one or more polymer chosen from polyolefins, cyclic olefin copolymer, polycarbonate, $SiO_2$ coated polymer, polyethylene, and/or plastic completely or partially covered in metal;
   ceramic; and/or
   metal.

40. The medical apparatus of claim 22, wherein the one or more first protective container comprises one or more of:

reusable, recyclable, and/or compostable material(s); and/or renewable or fossil oil based raw material(s).

41. The medical apparatus of claim 22, wherein the one or more first protective container is coated with one or more of:
   moisture resistant agent(s);
   moisture impermeable agent(s); and/or
   sterilization impermeable agent(s).

42. The method of claim 1, wherein an interior of the second protective container comprises an antimicrobial agent.

43. The method of claim 42, wherein the antimicrobial agent is provided on and/or impregnated in a substrate.

44. The medical apparatus of claim 22, wherein an interior of the second protective container comprises an antimicrobial agent.

45. The medical apparatus of claim 44, wherein the antimicrobial agent is provided on and/or impregnated in a substrate.

* * * * *